United States Patent
Brady et al.

(10) Patent No.: US 6,417,004 B1
(45) Date of Patent: Jul. 9, 2002

(54) ENHANCING CLOT DETECTION IN ACTIVATED CLOTTING TIME AND OTHER FIBRIN ENDPOINT BASED TESTS

(75) Inventors: Terry E. Brady, Gladstone; Michael F. Corsello, Bridgewater, both of NJ (US)

(73) Assignee: Helena Laboratories Corporation, Beaumont, TX (US)

(*) Notice: Subject to any disclaimer, the term of this patent is extended or adjusted under 35 U.S.C. 154(b) by 0 days.

(21) Appl. No.: 09/503,260

(22) Filed: Feb. 14, 2000

Related U.S. Application Data (60) Provisional application No. 60/131,535, filed on Apr. 29, 1999.

(51) Int. Cl.⁷ .............................................. G01N 33/86
(52) U.S. Cl. ..................... 436/69; 436/149; 436/150; 436/157; 422/73; 73/64.41
(58) Field of Search ........................... 436/63, 69, 149, 436/150, 151; 422/68.1, 73; 73/64.41

(56) References Cited

U.S. PATENT DOCUMENTS

| | | | | |
|---|---|---|---|---|
| 3,695,842 A | * | 10/1972 | Mintz | 436/150 |
| 3,836,333 A | * | 9/1974 | Mintz | 422/73 |
| 4,189,382 A | * | 2/1980 | Zine, Jr. | 210/714 |
| 5,091,304 A | | 2/1992 | La Duca et al. | 435/13 |
| 5,110,727 A | * | 5/1992 | Oberhardt | 435/13 |
| 5,154,082 A | * | 10/1992 | Mintz | 73/64.41 |
| 5,350,676 A | * | 9/1994 | Oberhardt et al. | 435/13 |
| 5,670,329 A | * | 9/1997 | Oberhardt | 435/13 |
| 6,136,271 A | * | 10/2000 | Lorincz et al. | 422/73 |

* cited by examiner

Primary Examiner—Maureen M. Wallenhorst
(74) Attorney, Agent, or Firm—Piper Rudnick LLP; Jerold I. Schneider

(57) ABSTRACT

The present invention is directed to a method and apparatus for detection of a diagnostically significant amount of clot in an aliquot of blood. In a preferred embodiment, the method uses a cocktail of activators to facilitate and proctor absolute activation of Factor XII (the contact factor for the intrinsic pathway of coagulation). Possible activators include Celite®, kaolin, glass beads, colloidal silica, and diatomaceous material. This cocktail formulation is important because some individuals respond differently to different activators and hence, the cocktail formulation facilitates standardization of the patient population by reducing the patient-activator sensitivity artifacts.

14 Claims, 4 Drawing Sheets

ENHANCING CLOT DETECTION IN ACTIVATED CLOTTING TIME AND OTHER FIBRIN ENDPOINT BASED TESTS

This application claims the benefit of U.S. Provisional Application Ser. No. 60/131,535, which was filed on Apr. 29, 1999.

BACKGROUND

During cardiopulmonary bypass (CPB) for open-heart surgery, the patient's blood is circulated into an extracorporeal circuit. The non-biological surfaces of the bypass circuit are known to exhibit a strong procoagulant effect on the circulating blood. To offset this biological reaction, anticoagulants are routinely administered; the most common of which is heparin. Heparin is usually administered in high concentrations during periods of extracorporeal circulation. During these procedures, the Activated Clotting Time (ACT) and other endpoint based coagulation assays are frequently used to monitor these high levels of heparin and other coagulation parameters.

Blood clot formation is a complex phase. Several principles are useful in understanding fluid-phase coagulation. In general, the clotting proteins circulate normally as inactive precursors. Coagulation involves a series of activation reactions that in turn act as the catalysts for the next level of reactions and hence, the frequent term Coagulation Cascade. During the reaction(s) process, these proteins and the fibrin mass itself, is highly unstable and water-soluble. This will remain until the very final aspects of coagulation. In addition, without (or in limited quantities) those clotting proteins (or in the presence of anticoagulants, i.e., heparin), clotting becomes delayed or prolonged. Eventually, however, fibrin (the foundation of a blood clot) will be formed. This occurs with the cleaving of fibrinogen, one of the coagulation proteins. Finally, Factor XIII (stabilizing factor) is activated by thrombin to yield cross-linked fibrin, which is highly insoluble and stable in formation.

In 1966, Dr. Paul Hattersley, a physician from California, outlined the design and usage of a fresh whole blood clotting test utilizing a particulate for contact activation. This was to facilitate rapid test conclusion in a clinically meaningful timeframe. The test Hattersley described included placing 1 ml or more of blood into a tube prefilled with 12 mg of activator (diatomaceous earth, Celite®). This tube was pre-warmed to 37 degrees C. prior to administration of the patient blood sample. A timer was started when blood first entered the test tube. The tube was filled, and inverted a few times to accommodate mixing. The tube was then placed into a 37 degree C. water bath. At one minute and at every 5 seconds thereafter the tube was removed from the water bath and tilted so that the blood spread the entire length of the tube. The timer was stopped at the first unmistakable signs of a clot.

Shortly thereafter, automated methods based on the original Hattersley ACT were developed. Using several different techniques, all offered automated temperature management, automated end point detection, and automated timing counters. All of these automated ACT systems terminated the testing cycle when a significant clot mass was formed. This clot mass needed to be of sufficient size and strength to displace a ceramic magnet in a test tube and the displacement was detected by actuation of a magneto-mechanical switch. Of note, almost thirty years has elapsed with no fundamental improvement to this clot detection principle.

Over those thirty years, surgical techniques have changed greatly. Many complicating factors now exist that may induce artificial error in ACT test systems that require a strong blood clot to trigger the clot detection mechanism. These variables include deep hypothermia, new platelet preservation/enhancement drugs (aprotinin, DDAVP, transexamic acid), thrombolytics, antiplatelet compounds, and a series of new opiates, benzodiazapenes, and analgesics.

For almost three decades, electromechanical ACT clot detection mechanisms have been the mainstay of ACT testing systems. Throughout that time, they have undergone no fundamental change.

In the early 1960's, a saline-rinsed ACT test tube was manufactured to work on an automated instrument for determining the ACT on routine heparinized patients. This was designed to specifically supercede the manual Lee-White Clotting time (a non-activated whole blood clotting test that predated Hattersley's ACT). The instrument, called HEMOCHRON® (International Technidyne Corporation, Edison, N.J.) employed a single point electromechanical clot detection mechanism for identifying clot end-point in these heparinized samples. The mechanics behind this clot detection system were simple, yet effective. They are disclosed in U.S. Pat. No. 3,695,842, issued Oct. 3, 1972 and a further development thereof is disclosed in U.S. Pat. No. 5,154,082, issued Oct. 13, 1992.

Figure 1:
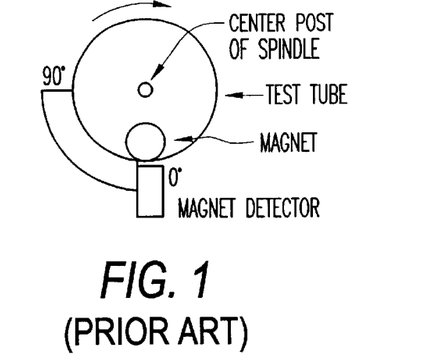
FIG. 1 illustrates a conventional magnet located in the center post of a spindle within a test tube as described in the prior art.
Figure 2:
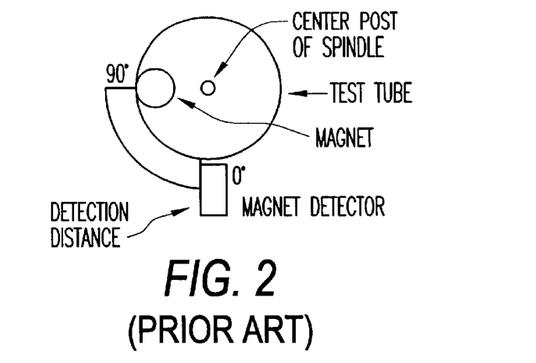
FIG. 2 illustrates a conventional electromechanical clot detection system as describe in the prior having a detection distance approximately 90 degrees from the bottom of the tube.

Inside each HEMOCHRON unitized test tube (along with the reagent or activator) is a magnetized ceramic bar. In order to minimize the change from the original Hattersley hand-held ACT to the automated ACT system, the magnetized ceramic bar was coated with a substance as to make it "invisible" to the blood. In other words, the magnet was intentionally treated to minimize thrombogenic capabilities. The ACT test tubes are inserted into the analyzer. and are held in the detection well at a 30-degree angle. This angle is used to proctor the reagent, patient sample and magnet placement to rest in the bottom of the test tube in close proximity to the tube center post. This center post provides the main adhesion point for the clot to assist in magnet displacement. In addition, at the top of the center post is a spindle. This spindle is designed to grab fibrin formation forming in the top of the blood sample. The spindle is placed well above the detection magnet in the test tube. It is important to note that this tube is designed to utilize large blood sample volumes, not reduced or micro volumes more accepted in medicine today. Once the tube is inside the well, the sample is heated to 37 degrees C. (body temperature) and the tube is rotated at a speed of 1 revolution per minute. As the blood in the tube remains liquid (unclotted), the magnet is free to roll in the bottom of the tube independent of the 1 revolution per minute tube rotation (FIG. 1). As the clot mass forms and solidifies, the clot mass binds the magnet and the tube center post and no longer allows the magnet to roll independently of the test tube. When the magnet reaches a fixed distance from the detector, the magnetic field is no longer sensed by the detector, the switch opens, and the instrument detects a clot. In traditional electromechanical clot detection systems, the detection distance is approximately 90 degrees from the bottom of the tube (FIG. 2).

Figures 3, 4:
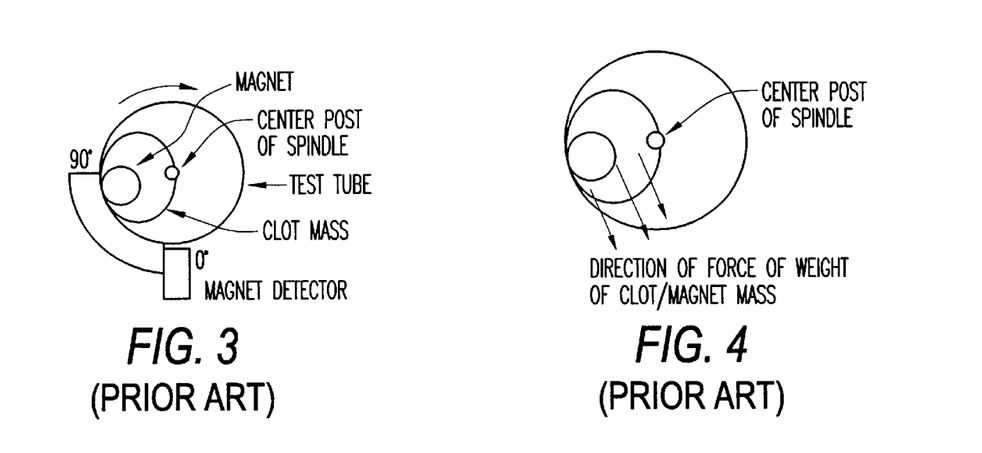
FIG. 3 illustrates the rotation to the 90 degree point in a conventional electro-mechanical clot-detection system.
FIG. 4 illustrates the direction of force of the weight of the clot and magnet mass in a conventional electromechanical clot detection system.

The detection distance is an important measurement. This measurement has direct correlation with the instrument's clot detection sensitivity, especially when a stable clot mass cannot be formed reliably. In reference to single detection point mechanisms, as described above, these are very susceptible to prolonged end point detection during high heparinization (i.e., bypass surgery) procedures. In these highly heparinized procedures, large amounts of anticoagulants are given to prevent fibrin formation. Despite the strong clot activators in the ACT tubes (celite, kaolin), this large amount of heparin (and subsequent hemodilution) usually prevents stable clot masses from forming consistently. As the clot begins to form in the tube, the clot mass, and its attachment to the center post, must be stable (strong or tight) enough to displace the magnet the minimal detector distance. As the magnet/clot mass travels this large distance along the rotation of the outer wall of the tube, the stability/strength of the clot mass must have the ability to bear the weight of the clot mass/magnet as it rotates to the 90-degree point (FIG. 3). As the mass approaches 90-degrees from the bottom of the test well, gravity begins to put stress on the mass. If the mass is not "strong" enough, or properly adhered to the wall of the test tube, the mass will "slide" back, and the detector will not signify the proper end of the clotting cycle despite the obvious formation of clot.

As the clot mass/magnet continues to rotate to the detection point, the stability of the mass must be great enough to bear its own weight (FIG. 4). If it cannot, it may simply "slide" back into the bottom of the tube, where the gravitation force on the mass is lowest, and return into the detection area. This is critical to accurate measurement of highly heparinized patients because even though a clot has formed, its stability is what is dictating the end point detection. This phenomena can be seen clinically as unusually high ACT results, unreliable results (poor reproducibility), and frequent tests that "time out" due to the detector's inability to distinguish a clot within the timing range of the instrument.

SUMMARY OF THE INVENTION

The present invention is directed to a method and apparatus for detection of a diagnostically significant amount of clot in an aliquot of blood. In a preferred embodiment, the method uses a cocktail of activators to facilitate and proctor absolute activation of Factor XII (the contact factor for the intrinsic pathway of coagulation). This cocktail formulation is important because some individuals respond differently to different activators.

DETAILED DESCRIPTION OF THE INVENTION

The overall design and implementation of the present invention is directed to the detection of a diagnostically significant amount of clot in an aliquot of blood specimen from a human or other mammal. This invention is based on the improved generation, adhesion, and concentration of the blood clot. According to the present invention, it is possible to vastly increase result integrity while decreasing the blood sample volume required for these analyses. This is done by incorporating several novel improvements to traditional ACT test system components, including the instruments and test tubes. In a preferred embodiment of the invention, these advancements effect the "binding" of the magnet and blood clot, thus improving clot detection.

CLOT ADHESION AND PROCOAGULANT SITES

Since traditional ACT tubes are either glass or plastic, their inner chambers are smooth polished surfaces. By increasing the "roughness" of the inside of the tube, it is possible to better facilitate blood clot formation and adherence capabilities of that blood clot to the tube walls. To accomplish this, texturing will be administered to the area of the inside of the tube, the magnet, or any component with which the blood has contact. This texturing provides "anchoring" points for the blood clot that is forming in the tube. In addition to providing anchoring sites for the blood clot, texturing will also exponentially increase the surface contact area of the reaction chamber. In addition, unlike previous detection magnets that are intentionally "buffered" from the reaction, by not treating the magnets, their naturally rough surface becomes an excellent adhesion and procoagulant site. The inside of the test tube disposables will be textured for better thrombogenicity and thromboadherence. These textures can be created in a multitude of fashions. They include, but are not limited to, texture molding, acid etching, or rough-particle etching. In molding, the texture pattern would be included in the mold of the test tube disposable. This allows for an array of different tubes each with individual texture surfaces for optimal performance. The acid and rough etching use chemicals or physical particulate respectively to etch the inside of the tube reaction area. This methodology is intended to yield a higher concentration of texturing in the tube than otherwise possible, due to molding limitations. Again, this will have beneficial affects on the quality and reliability of the blood clot being formed.

CENTER POST AND SPINDLE REMOVAL

By reengineering the traditional test tube disposable used for ACT testing, it is possible to remove the center post of the tube. Removal of this post is beneficial to overall reduction in both cost and manufactured parts and elimination of variance (hence the variable influence it may have) in placement of this spindle. The removal of this post is made possible by reestablishing the necessary sample fill, and by the increased thrombogenicity and thromboconcentration of the novel designs, discretely or in combination. With the increased adherence capabilities of these new designs, the traditional center post is no longer required for clot adherence purposes and the required blood samples can be reduced.

SYMBIOTIC RELATIONSHIP OF MULTIPLE PARTICULATE ACTIVATORS

It is probable that the Factor XII (contact factor for the intrinsic pathway of coagulation) is not always entirely specific to a single activator. In probability, it has discrete receptors to multiple specific activators. In addition, some of these receptors are likely to have specificity to only certain types of activators. Understanding this, it is important to vary the activators and the activation sites to initiate the reaction as dynamically as possible. To date, ACT tubes incorporate only a single particulate activator in either a glass or plastic vesicle. With the new understanding of the biology involved in Factor XII activation, it is desirable to create multiple "cocktails" of particulate activators in the disposable. This is to facilitate and proctor absolute activation of Factor XII in a majority of the patient population when using a variety of pharmaceuticals known to negatively affect certain, but not all, Activated Clotting Times. These activators can include, but are not limited to, celite, kaolin, glass beads, colloidal silica, platelet agonists, fibrinogen, and ellagic acid, in pairs or in multiple combination. Simple combinations of compatible but different activators can be added to the test system. An example of the many possible combination follows.

Figure 15:
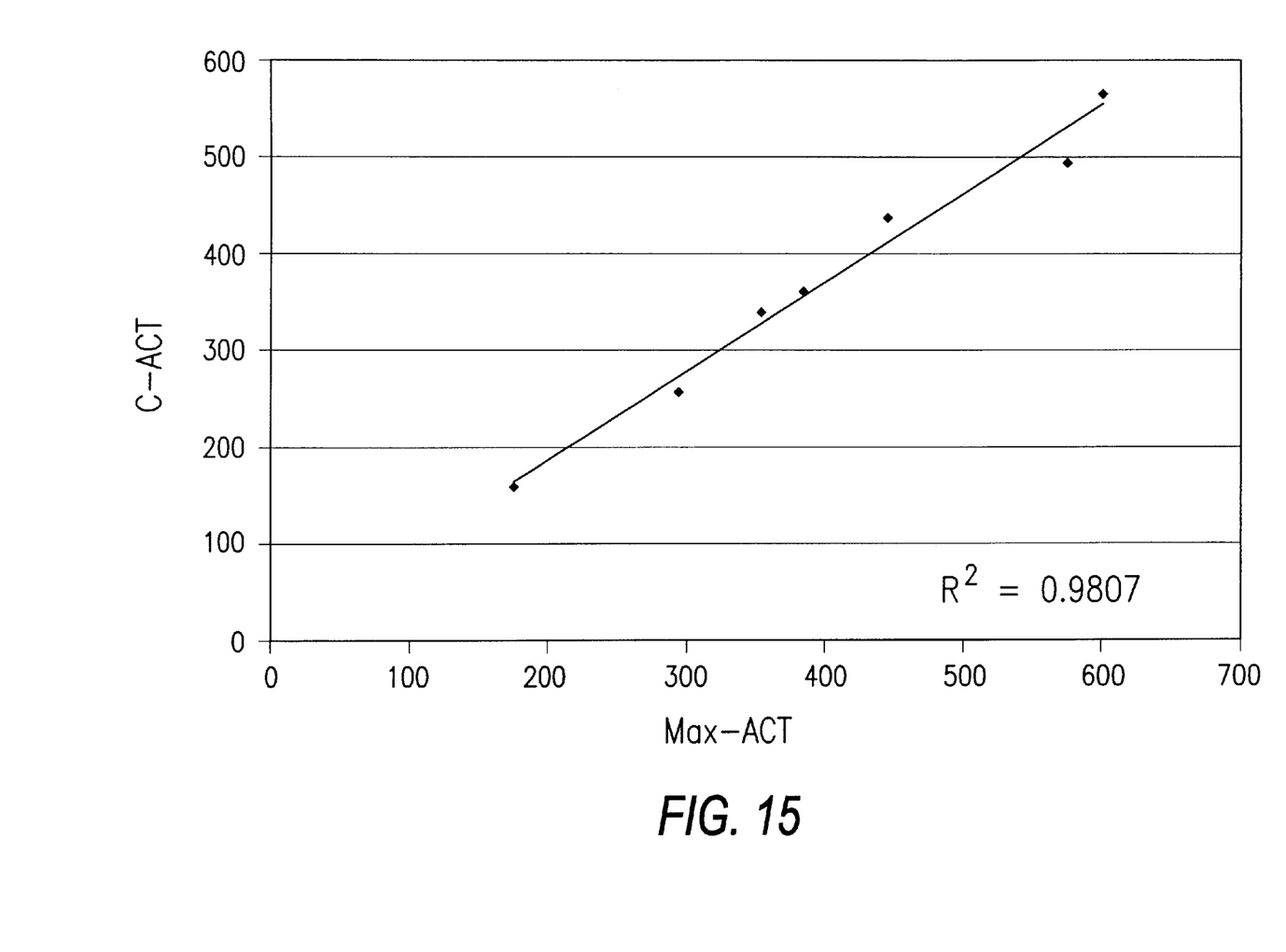
FIG. 15 illustrates the linear relationship of MAX-ACT versus C-ACT heparin.

Through use of a combination of particulate activators an exemplary ACT testing tube was developed that, using 1.0 milliliter of blood, accurately mimics the reference C-ACT tube that requires 2.0 milliliters of blood. The tube is a molded plastic tube with a molded center post. The novel activator "cocktail" is a 50 mg dispense consisting of 3.5 mg of celite, 3.5 mg of kaolin and 43 mg of glass beads. The tubes (MAX-ACT) were used to test the coagulation of blood from 6 normal healthy subjects. The data, showing as many as 8 measurements of clotting time (seconds) for each subject sample (Table 1), show a normal value and spread.

the clotting time (in seconds) as a function of heparin admixture in the blood sample, shows that the MAX-ACT results track the C-ACT results quite closely. The degree of tracking is demonstrated in FIG. 15, which shows a plot of C-ACT times v. MAX-ACT times at different heparin levels. The Tracking measure R2=0.9807, where R2=1.0 for perfect tracking.

Multiple activators may also be used to increase the sensitivity of the Activated Partial Prothrombin Time (APTT) test, since this test also depends on contact (Factor XII) activation in the presence of phospholipids.

Another method to accommodate multiple activator designs is to redefine the traditional filling techniques. These can be coupled (or used discretely) with novel advanced spray powdering techniques. By utilizing spray powdering in single reaction preparation, the spray powdering allows for activator adhesion/placement anywhere in the testing chamber (walls, magnet, top, bottom, etc). When creating tubes with multiple activators, to prevent reagent migration and homogenization (if not desired), it is possible to "place" reagent in specific regions of the reaction chamber with powdering techniques. These powdering techniques (with additional surfactant, such as a sucrose solution, to act as a "glue") allow the specific placement of the activator into a planned, specific location in the reaction chamber without reagent migration.

MAGNET RETENTION SITES (MRS)

Figure 7:
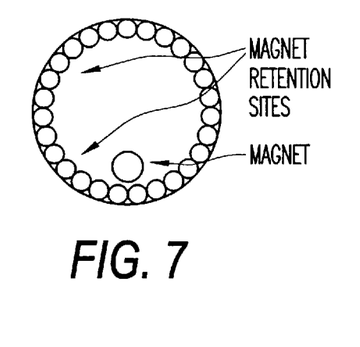
FIG. 7 is a cross-sectional view of a concentric longitudinal configuration for holding the magnetic in a specific place.
Figure 8:
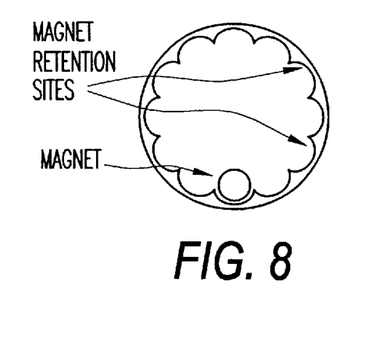
FIG. 8 is a cross-sectional view of a concentric longitudinal configuration for holding the magnetic in a specific place.

By changing from the traditional smooth concentric inner chamber of the test tube, it is possible to increase the surface area of the tube, therefore increasing the "sites" at which a blood clot will form and adhere. In addition to facilitating clot formation and adherence, it is also advantageous to facilitate the blood clot's formation to the proximity of the detection magnet. By designing concentric longitudinal "ripples" throughout the length of the test chamber, as illustrated in FIGS. 7 and 8, it is possible to "hold" the magnet in a specific place, for a specific time period (i.e., 1–3 seconds). In traditional ACT disposables, there is little surface contact between the magnet and the disposable. This is due to the physical geometry in which two cylinders, of different sizes (i.e. the magnet and tube), make mutual contact at only a small point. By utilizing the MRS design, the area of contact between the magnet and the test tube is effectively doubled or tripled. In addition, the traditional test

TABLE 1

Normal Range Study

|           | 1    | 2    | 3    | 4     | 5    | 6     | 7    | 8     | AVG     |
|-----------|------|------|------|-------|------|-------|------|-------|---------|
| Patient A | 142  | 134  | 134  | 125   |      |       |      |       | 134     |
| Patient B | 128  | 125  | 125  | 118   |      | 111   | 121  | 125   | 122     |
| Patient C | 120  | 124  | 112  | 119   | 119  | 121   | 116  | 117   | 119     |
| Patient D | 133  | 140  | 118  | 124   | 121  | 127   | 126  | 123   | 127     |
| Patient E | 141  | 143  | 132  | 130   | 133  | 136   | 136  | 142   | 137     |
| Patient F | 139  | 123  | 133  | 148   | 134  | 136   | 137  | 139   | 136     |
|           |      |      |      |       |      |       |      |       |         |
| Avg       | 134  | 132  | 126  | 127   | 127  | 126   | 127  | 129   | 128     |
| SD        | 8.61 | 8.73 | 9.05 | 11.02 | 7.85 | 10.62 | 9.20 | 10.78 | 7.73    |
|           |      |      |      |       |      |       |      |       | 105.151 |

Figure 14:
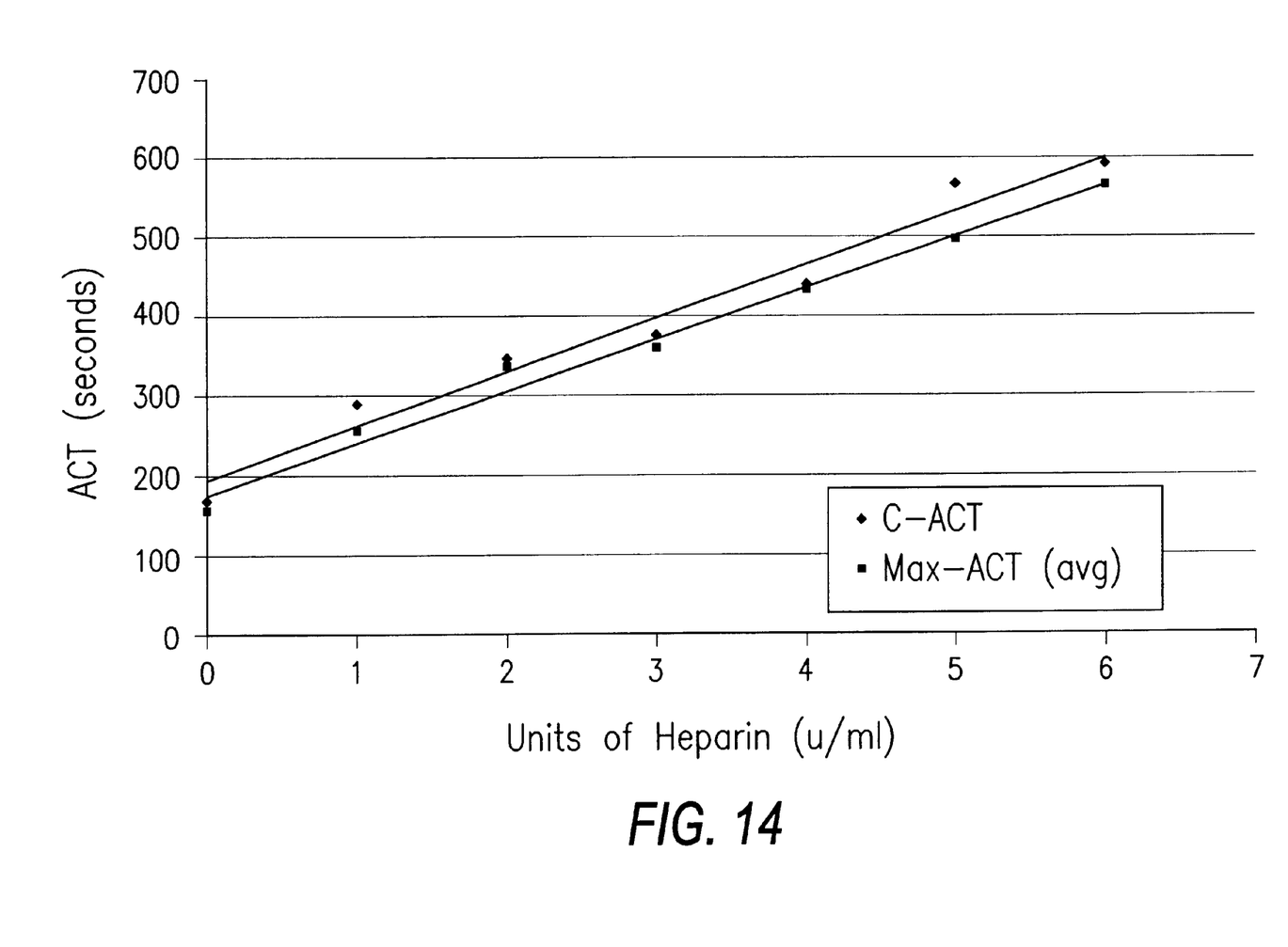
FIG. 14 illustrates the linear relationship of MAX-ACT™ versus C-ACT heparin.

A series of tests was then run to compare heparinized blood clotting time measurements using the MAX-ACT tubes with clotting time measurements using the standard C-ACT tubes at different heparin levels. FIG. 14, showing tube rotates at a constant 1 rotation per minute during the test cycle. This allows the magnet to continuously roll within the test tube. This constant motion allows little time interaction between the forming blood clot, the test tube wall and the magnet. Lack of this interaction time (due to the constant magnet shifting due to the normal rolling motion of the tube) hinders the bloods ability to form a solid, stable clot. With the MRS design, it is possible to stagnate the magnet motion, only momentarily, but long enough so that the blood clot (fibrin strands) has an opportunity to adhere to the Clot Retention Sites on the wall of the tube, as well as the ceramic magnet in the tube.

Figure 9:
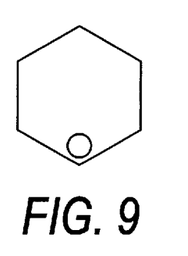
FIG. 9 is a cross-sectional view of a magnetic retention site with multi-faced tube.
Figure 10:
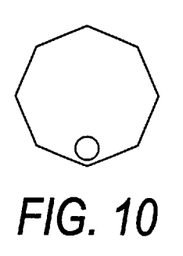
FIG. 10 is a cross-sectional view of a magnetic retention site with multi-faced tube.
Figure 11:
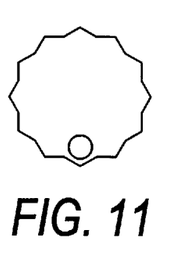
FIG. 11 is a cross-sectional view of a magnetic retention site with multi-faced tube.

In addition, it is also possible to accomplish similar outcomes using a multiple faceted tube. Instead of using the traditional cylindrical test tube, it is possible to achieve the same goals as the MRS design above using these new tubes. These multifaceted tubes can have up to thirty discrete sides or as few as six (See FIGS. 9, 10, and 11).

NEW CLOT DETECTION MECHANISM

The present invention provides a new methodology for clot detection that improves both the standardization and reproducibility for clot detection. Unlike the single point detection mechanism that has been conventionally used, the present invention uses a multi-point detection system (called the Actalyke® system) that "tracks" the movement of the magnet within the test chamber. By utilizing algorithms and a plurality of detection points, it is possible for the new detection premise to "triangulate" and calculate the position and movement of the magnet. This allows the Actalyke system to closely mimic the clotting times of the single point method under normal circumstances, but it is not susceptible to the abnormal prolongation frequently associated with "weak or unstable" clots.

Figures 5, 6:
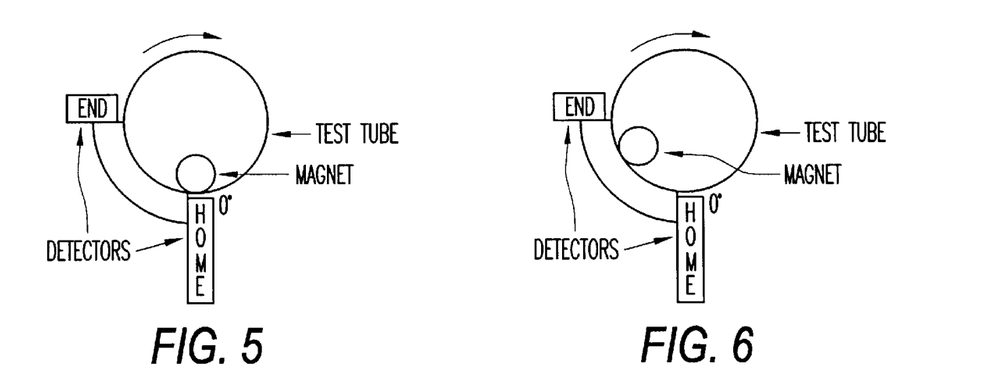
FIG. 5 illustrates the position of the magnet in the bottom of the tube independent of the tube rotation.
FIG. 6 illustrates the location and movement of the magnet approximately 46 degrees from the HOME detector.

The new detection system utilizes a multi-point magnet detector network and sensitive magnetic field measuring devices. Each unitized test tube (along with the reagent or activator) contains a magnetized ceramic bar. The ACT test tubes are held inside the detection well at a 15-degree angle. After blood is placed into the ACT test tube, it is placed into the test well. Once inside the test well, the sample is heated to 37 degrees C. (body temperature) and the tube is rotated at a speed of 1 revolution per minute. As the blood in the tube remains liquid (unclotted), the magnet is free to roll in the bottom of the tube independent of the 1 revolution per minute tube rotation (FIG. 5). As the clot mass forms and solidifies, the clot mass binds the magnet and no longer allows the magnet to roll independently of the test tube. When the magnet reaches a specific distance, approximately 46 degrees from HOME detector, (or one degree closer to END detector than the HOME detector), the detection systems, in tandem, identify the location and positive, logical movement of the magnet and signify an "end-point" (FIG. 6). The magnetic fields can be measured using Hall-effect detectors or other known magnetic field detection devices.

By using multiple, networked detection systems, logic "gates" or conditions must be met for the instrument to determine a true clot formation (fibrin generation) without stability biases. These gates include logic (algorithms) in regard to ceramic magnet location, movement rate, direction, and cessation rate. In essence, by using logic in this form of clot detection, we can identify positive movement of the magnet caused by the presence of fibrin strands (soft clot), and alleviate error caused by variable, delayed hard clot formation and/or errors (such as air bubbles).

LOGIC GATES

The Actalyke instrument can incorporate numerous logic gates or algorithms into its detection process to improve clot detection and minimize testing error. This can include, but is not limited to, rate tracking of the magnet motion, and magnet motion cessation. By including a rate tracking algorithm it is possible to "watch" the motion of the magnet in the testing vesicle for motion change caused by fibrin strands. For example, as fibrin strands form in the testing vesicle, they will be distributed and deposited on the backside of the magnet due to the normal rotation to the test tube. These fibrin strands will have a motion effect on the magnet in the vesicle. When the strand concentration is sufficient, it will provide a mass behind the magnet. This mass will push the magnet clockwise due to the rotation of the tube. By trending this "pushing" of the magnet due to a fibrin strand mass, it is possible to positively identify positive motion due to a mass and conclude the mass is of blood fibrin strand origins. Since the mass can only "push" the magnet at the same speed as the rotation of the testing vesicle (1 rotation per minute) it is possible to "filter" out abnormal magnet influences in cases where the magnet is moving too fast. This can help alleviate false endpoints due to air bubbles or abrupt instrument movement or jarring. By the same token, if the motion of the magnet can be established and tracked, it is also possible to identify the point in time in which there is cessation of movement of the magnet. Algorithms and logic gates such as these have huge implications on removing error and increasing overall testing integrity.

This advancement in clot detection mechanisms will be noticed immediately in numerous clinical settings in the form of increased reproducibility. In higher heparin environments, the Actalyke system will be much less affected by unstable clot masses than single detection point systems and their inherent prolongation.

ADVANCED PROCOAGULANT TECHNIQUES

As with all end-point fibrin based tests, there are many advantages to facilitating superior procoagulant capabilities of the test. In addition to increasing the texture, hence surface area of the contact area (as disclosed previously), there are several other techniques which can be used, either discretely or in combination, to promote procoagulation. The techniques described below are based on manipulation, preparation, and utilization of the activator to be used within the testing chamber.

To increase procoagulant abilities and general clot formation and stability, the addition of a platelet agonist can be utilized. By utilizing a platelet agonist, the platelets in the sample can be prompted to activate. After activating, the platelets react with the fibrinogen in the sample (or added as a reagent accelerator discussed below) to assist in forming fibrin, which resembles tiny threads. The fibrin threads then begin to form a web-like mesh that traps the blood cells within it. These actions, coupled with the normal clotting process taking place within the reaction chamber due to intrinsic (or extrinsic) activation, will facilitate clot formation (procoagulation).

As discussed above, there are advantages to the addition of fibrinogen or other procoagulants (a coagulation factor) to end-point fibrin based clotting tests. As stated above, there is positive interaction between platelets (endogenous or exogenous to the sample) as well as fibrinogen's contribution to normal intrinsic (or extrinsic) activation and subsequent clot formation. Techniques of utilizing fibrinogen include spray powdering techniques previously described and ionic covalent binding. Since the role of the ceramic magnet in these types of tests is critical (it is the magnet's actual participation in the blood clot that ends the testing cycle), any procoagulation techniques described here have immediate consequences if applied directly to that ceramic magnet. By ionically binding fibrinogen to the magnet, all procoagulation effects yielded from the addition of the fibrinogen are concentrated and centralized into the area of test influence (magnet displacement).

BLOOD VOLUMES

Currently, ACT tests designed for high heparin (therefore subjected to weak clots) use 2.0 ml of fresh whole blood from the patient. It is our goal to create these new tubes to utilize lower blood volumes. In our experience, with these novel designs, it should be possible to create ACT tubes that utilize blood volumes of between 2.0 ml and 0.25 ml, preferably less than 1.0 ml.

ADVANCED MAGNET DESIGN AND TECHNIQUES FOR CLOT PROCOAGULATION, ADHESION, AND CONCENTRATION (THE ARRAY PRINCIPLE)

As previously discussed, the magnet plays a vital role in clot detection. As the blood is liquid (unclotted), the magnet "rolls", clockwise with the tube rotation, until the blood solidifies, binding the magnet and the tube. Further rotation of the "clotted" magnet reaches an end point in the detection mechanism. Understanding this, again, any novel design improvement made to the detection ceramic magnet in the sample will have direct effect on the integrity of the test being performed. As previously discussed, there are advantages to increasing the surface area of the activator and non-biological surfaces contacting the blood. This promotes maximum blood activation. By incorporating textures on surfaces, these sites provide "snag" sites for blood clot strands (fibrin) to facilitate clot adhesion. By using spray powdering, and ionic binding, it is possible to make a specific aspect or location of the test chamber "hotter" or more active (from a procoagulant perspective) than another part. This is essential in facilitating blood clot formation in an area with immediate ramification. When these principles are collectively applied to the detection ceramic or metallic magnet, it is defined as the Array Principle.

Figure 12:
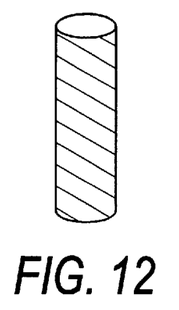
FIG. 12 illustrates an enhanced detection ceramic magnet.
Figure 13:
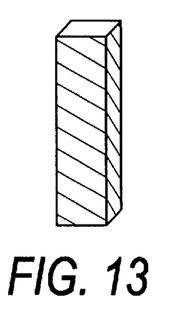
FIG. 13 illustrates an enhanced detection ceramic magnet.

By incorporating a novel magnet approach into endpoint fibrin-based clotting tests, the overall integrity, sensitivity, and reproducibility of the test being performed is enhanced greatly by facilitating the instrument's ability to recognize the formation of the blood clot. In a preferred embodiment of the invention based on the Array Principle, there is a ceramic polarized magnet or magnetically polarized spiral body. By incorporating either a positive or negative surface design in the shape of a counterclockwise corkscrew (illustrated in FIGS. 12 and 13) on the surface of the magnet (on the individual faces of a multifaceted magnet or on the cylindrical face of a cylindrical magnet), it is possible to do the following: (1) increase the surface area contact between the blood sample, tube wall, and test magnet (increased contact increases procoagulation or thrombogenicity), (2) provide an area due to the positive or negative sites on the magnet for increased adhesion of the forming blood clot and (3) facilitate the migration of premature blood clots (fibrin strands) to the bottom of the testing chamber for concentration due to the physical nature of a corkscrew design on a rolling (unclotted) magnet. In that specific location, it is possible for the concentration of these fibrin strands to stabilize and solidify, attach to any of the tube or magnet adhesion sites, and have direct impact on the binding (clotting) of the magnet and the tube bridged by the coagulated patient blood sample being tested. It is also noteworthy that one can change the geometry of the magnet to increase the surface area and enhance coagulation adhesion characteristics. Additionally, a magnetized spiral body, in the shape of the columnar magnet, may also be substituted.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus and method may be varied substantially without departing from the spirit of the invention and the exclusive use of all modifications that come within the scope of the appended claims is reserved.

What is claimed is:

1. A method for detection of a diagnostically significant amount of clot in an aliquot of blood comprising:
    a) adding said aliquot of blood to a blood-clotting test tube which contains therein a rotatable magnetically polarized body with a textured surface;
    b) mixing the blood with a non-biological, non-soluble particulate contact activator in the tube;
    c) maintaining the tube at a predetermined angle to the horizontal and rotating the tube about the axis of the tube at a predetermined rate;
    d) detecting the magnetic field produced by the magnetically polarized body by means of a plurality of magnetic detectors, each producing an electrical signal corresponding to the strength of the magnetic field at the position of that detection; and
    e) determining the position of the magnetically polarized body within the tube by comparing the plurality of electrical signals wherein movement of the magnetically polarized body from a non-clotted position indicates a diagnostically significant amount of clot in the aliquot of blood.

2. The method of claim 1 wherein the contact activator comprises a plurality of particulate activators.

3. The method of claim 2 wherein the activators are selected from the group consisting of celite, kaolin, glass beads, colloidal silica, and diatomaceous earth material.

4. The method of claim 1 further comprising controlling the placement of said activator within the tube.

5. The method of claim 1 further comprising increasing the texturing within said tube.

6. The method of claim 5 wherein increasing the texturing includes increasing the surface area of said tube.

7. The method of claim 5 wherein increasing the texturing includes increasing the surface area of said activator.

8. The method of claim 5 wherein increasing the texturing includes molding or etching the tube.

9. The method of claim 1 wherein the volume of the aliquot of blood is about 0.25 ml to 2.0 ml.

10. The method of claim 1 wherein the volume of the aliquot of blood is less than about 1.0 ml.

11. An apparatus for detecting a diagnostically significant amount of clot in an aliquot of blood comprising:
    a blood-clotting test tube for containing the blood;
    a rotatable magnetically polarized body within said tube wherein the surface of the body is textured;
    means for holding the test tube at a predetermined angle to the horizontal;
    means for rotating the test tube about its axis at a predetermined rotation rate;

a plurality of magnetic field detectors disposed around the test tube positioned in proximity of the magnetically polarized body, each detector adapted for producing an electrical signal corresponding to the strength of the magnetic field at that detector;

means for comparing the plurality of electrical signals to determine the position of the magnetically polarized body within the test tube; and means for correlating the position of the magnetically polarized body with a mass of the clot.

12. The apparatus of claim 11 wherein the inner surface of the tube is textured.

13. The apparatus of claim 11 wherein the magnetically polarized body is spiral-shaped.

14. The apparatus of claim 11 wherein the test tube has a cross-section defined by an array of protuberances for temporarily stopping the motion of the magnetically polarized body to increase adherence of the clot to the tube and the body.

* * * * *